Sept. 16, 1947. O. E. FELTEN Plant Pat. 761
STRAWBERRY PLANT
Filed Aug. 5, 1946
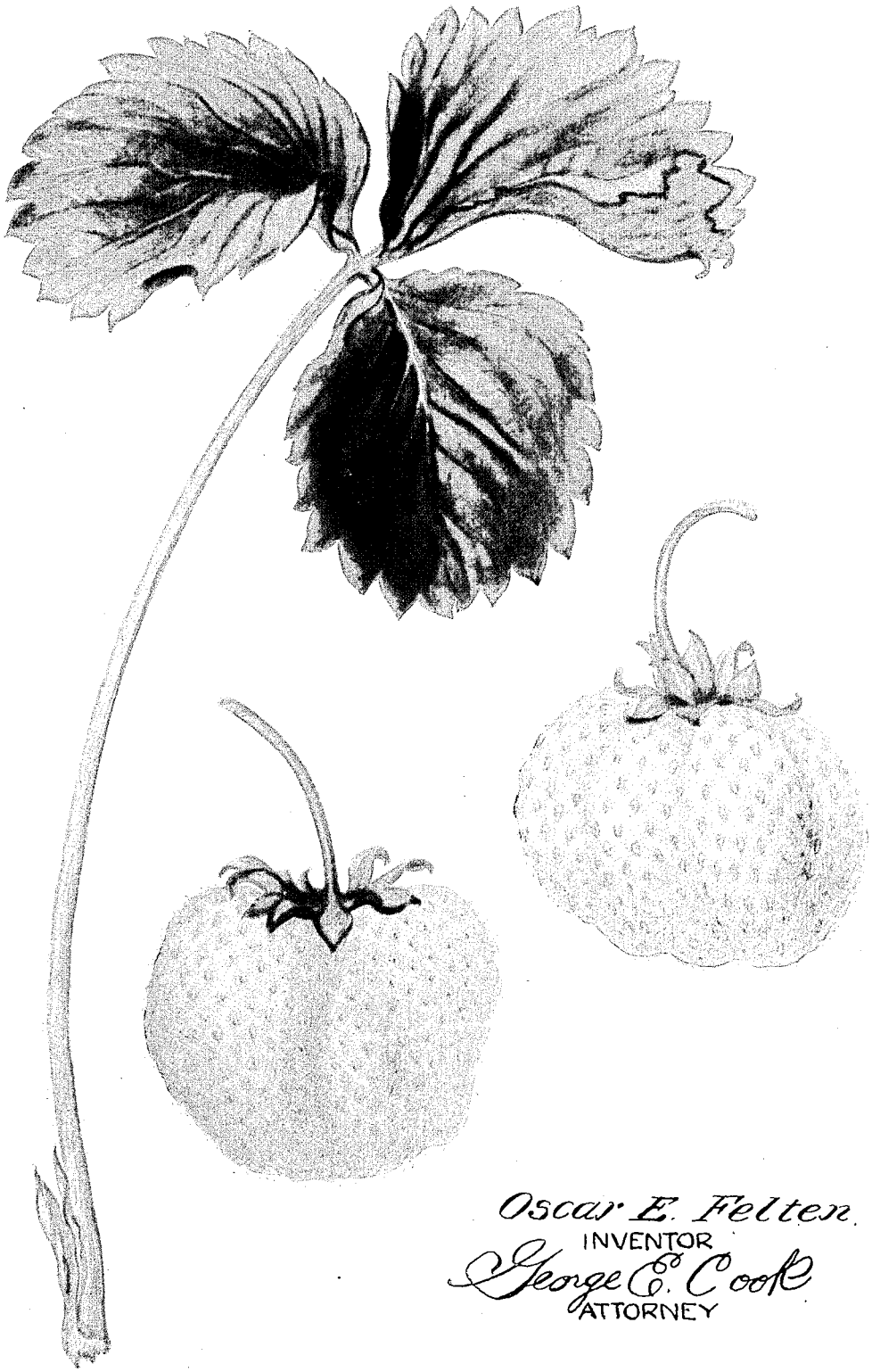
Oscar E. Felten
INVENTOR
George C. Cook
ATTORNEY Patented Sept. 16, 1947

Plant Pat. 761

UNITED STATES PATENT OFFICE

761

STRAWBERRY PLANT

Oscar Earle Felten, East Merchantville, N. J.

Application August 5, 1946, Serial No. 688,534

1 Claim. (Cl. 47—62)

My present invention relates to improvements in strawberry plants. The object of my invention is the production of a strawberry variety which is vigorous and healthy, productive of large plants, and also productive of a good quantity of berries having the highly marketable combination of large size, attractive appearance, quality of taste, and good shipping characteristics. All these have been accomplished in my new variety, and asexual reproduction of the variety for several years has shown these qualities to be firmly fixed.

My new variety is the result of definite breeding efforts begun by me in 1921. Its direct parentage is Fairfax and an unnamed seedling developed in 1930 and noted to be an outstanding seedling among the hundreds which I had produced. The new variety is more like the parent Fairfax than any other variety known to me, but differs in many respects.

The accompanying illustrations show a leaf and the two characteristic types of berries of this variety, in approximately their true colors.

In the following detailed description, color plate references are to Ridgway's Color Standards and Nomenclature. Color names used without plate references indicate the ordinary dictionary use of the term.

*The plant*

Type: Self-pollinizing. Blossoms or flowers are "perfect" large and white, with center bordering on yellow.

Growth: Tall, strong and upright; produces very large plants which space well in the rows; thrives well in most types of soil.

Root system: Strong, heavy and vigorous.

Runners: Heavy, with long nodes. Number of runners is only moderate, thus avoiding matting in the row.

Disease resistance: Apparently the variety is free from root-rot, leaf curl, and leaf spot. No virus diseases have ever been noted on any of the plants.

Production habit: Very heavy producer of very large berries. Each plant produces a number of fruit stems, each bearing from 5 to 8 berries. There are frequently lateral branches bearing several berries each.

Maturity season: Produces in mid-season—about the time of Fairfax.

Fruit stems: Strong and about as long as leaf petioles. Remain upright until berries begin to ripen, when the great weight of the berries causes them to bend.

Foliage:

*Quantity.*—Abundant.

*Color.*—Medium green, approximately Forest Green (Pl. XVII). Foliage remains evergreen throughout the winter in this latitude.

*Size.*—Central leaflet averages 2½ inches long by 2⅛ inches wide; the two lateral leaflets are slightly smaller.

*Shape.*—Trifoliate, with short stalklets. Each leaflet is almost round and slightly undulate. Edge is cut with more or less irregular scallops. Both the leaves and the serrations of them are more rounded than are the usual strawberry leaves.

*Petiole.*—Six to eight inches long; heavy and upright; ciliate.

*The Fruit*

Shape: Wedge shaped, conical with heavy shoulder, and conical berries are found on this variety. The first berry on a bunch is usually very large. Some of the first berries are wedge shaped, some conical with a heavy shoulder and some conical. The wedge shaped berry is thicker than the usual berry of that type. Later berries are usually conical.

Size: Very large, some of the wedge shaped berries are seven (7) inches or more in circumference. Many of the first berries measure two (2) inches wide and two (2) inches long. Many of the shouldered conical berries are two (2) inches long and almost two (2) inches across at the shoulder.

Aspect: Very glossy until overripe.

Color: Medium light, approximately Peach Red (Plate I) at picking stage. When the berries become overripe they get very dark red.

Flesh:

*Flavor.*—Sweet but sprightly, rich strawberry flavor.

*Texture.*—Fine grained.

*Firmness.*—Medium.

*Juiciness.*—Very great.

*Color.*—Approximately the same color as the outside of berry, with a characteristic white streak surrounding the core. In the conical berries this white streak forms a heart shape.

*Seeds.*—Large and near the surface of the berry, thus protecting it.

*Calyx.*—Medium sized. Consists of 16 to 18 sepals on the wedge-shaped berries and 10 to 12 on the conical berries. Grows close to hub. Adheres well. Lies almost flat on conical specimens and is somewhat imbedded on the wedge-shaped berries.

*Comparison*

The variety most like my new variety is Fairfax, one of its parents. However there are a number of differences, principal of which are as follows:

1. Growth of the two varieties is similar except that the plants of my new variety are larger and stronger.

2. My new variety is a much heavier bearer than Fairfax.

3. Picking season is longer than Fairfax and later berries hold up in size much better.

4. Leaves of my variety are more nearly circular.

5. My new variety produces much larger berries.

6. Flavor of the berry of my variety, although similar to that of Fairfax, is a little more tart.

7. Berries of my new variety are more juicy and slightly less firm.

8. Color of the berries of my new variety is lighter than that of Fairfax berries.

Having thus disclosed my invention, I claim:

The new variety of strawberry plant, substantially as herein shown and described, characterized particularly by the vigor, health and good spacing of its very large plants; its prolific production of fruit; and its fruits combining large size, bright red color, sprightly flavor, and flesh of sufficient firmness to ship well.

OSCAR EARLE FELTEN.